United States Patent [19]

Goodman

[11] Patent Number: 4,567,880
[45] Date of Patent: Feb. 4, 1986

[54] ENDOSCOPIC DEVICE WITH THREE-WAY VALVE

[76] Inventor: Tobias M. Goodman, Noyes Neck Rd., Weekapaug, R.I. 02891

[21] Appl. No.: 686,300

[22] Filed: Dec. 26, 1984

[51] Int. Cl.⁴ .............................................. A61B 1/06
[52] U.S. Cl. ........................................................ 128/7
[58] Field of Search ..................................... 128/4, 6, 7

[56] References Cited

U.S. PATENT DOCUMENTS 3,791,379  2/1974  Storz ....................................... 128/4
4,263,897  4/1981  Terayama ................................ 128/7

*Primary Examiner*—William H. Grieb
*Attorney, Agent, or Firm*—Salter & Michaelson

[57] ABSTRACT

An endoscopic device comprises a tubular endoscopic sheath which has distal and proximal ends and is receivable in a patient, a telescope portion in the sheath, and an irrigation and drainage valve mounted on the device adjacent the proximal end of the sheath. The telescope portion is operable for viewing an area of a patient adjacent the distal end of the sheath and the valve is operable for effecting irrigation and drainage of the same area to provide improved visibility through the telescope portion. The valve is operable by moving a forefinger in a single motion across a knob portion of a valve element of the valve to move the valve element between a first position for effecting irrigation, a second closed position, and a third position for effecting drainage. The simple operation of the valve allows an operator to effect irrigation and drainage while viewing through the telescope portion and permits irrigation and drainage to be accurately controlled so that the risks to the patient are minimized.

5 Claims, 5 Drawing Figures

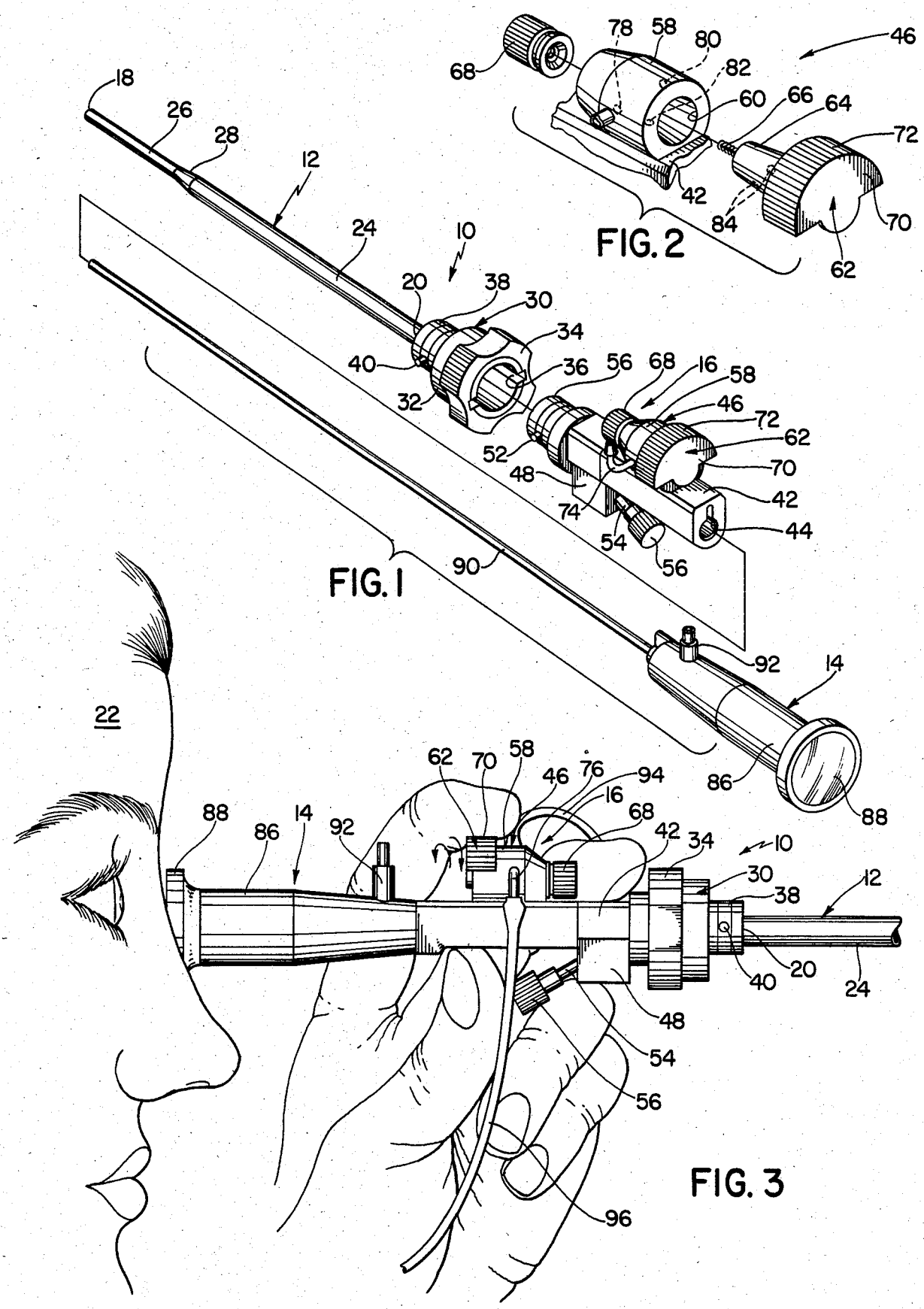

ENDOSCOPIC DEVICE WITH THREE-WAY VALVE

BACKGROUND AND SUMMARY OF THE INVENTION

The instant invention relates to medical instruments, and more particularly to an endoscopic device which is receivable in a patient for viewing internal organs therein, and for performing diagnostic and/or surgical procedures on the patient.

The use of various types of endoscopic devices for performing diagnostic and/or surgical procedures on various parts of the human body has been generally known in the medical field for a number of years. Further, it has been generally recognized that many times treatments which are performed on patients utilizing endoscopic devices cause substantially less trauma to the patients than similar treatments which are carried out utilizing conventional surgical procedures. Although some types of procedures which are carried out utilizing endoscopic devices do require relatively minor incisions to be made in patients in order to gain access to certain organs, many other procedures can be carried out through the normal body cavities and require little or no cutting of tissue, so that frequently they can be performed without causing any significant tissue damage. In contrast, corresponding procedures which are carried out utilizing conventional surgical techniques frequently require large incisions to be made in patients, and this obviously causes substantial tissue damage and substantially increases both the trauma and risks to the patient.

Generally, most endoscopic devices comprise a tubular outer sheath which has distal and proximal ends and which is receivable in a patient so that the distal end is located adjacent an area of the body of the patient to be treated or observed, and a telescope portion which is received in the sheath for viewing the area of the patient adjacent the distal end of the sheath. Preferably, a device of this type also includes means for irrigating and draining the area of the body of the patient adjacent the distal end so that clearer viewing of this area can be provided with the telescope portion. Further, in many cases, a device of this type may also include one or more appliances which are receivable in the sheath and are operable from a point adjacent the proximal end thereof for carrying out surgical procedures in the area of the body of the patient adjacent the distal end of the sheath. Although in some cases minor incisions must be made in patients in order to install endoscopic devices therein, in many cases, devices of this general type can be installed in patients without making incisions. For example, when performing diagnostic and/or surgical procedures in the lower urinary tract, an endoscopic device can generally be installed in a patient through the lower urinary tract itself, and hence an incision to accommodate the device is not necessary. In this connection, reference is made to the applicant's co-pending U.S. Pat. Application Ser. No. 525,620 entitled Ureteroscope, wherein an endoscopic device which is adapted for use in performing procedures in the ureter is disclosed and the operating procedures therefor are generally described. On the other hand, when treating and/or diagnosing disease processes in other organs which are not accessible from the body cavities, minor incisions must be made in order to install endoscopic devices, although generally, the incisions which are required to accommodate devices of this type are relatively small so that the trauma to a patient can nevertheless be minimized.

After an endoscopic device has been installed in the body of a patient, unimpaired direct visualization of the areas of the body adjacent the distal end of the sheath of the device is important for the effective performance of both surgical and diagnostic procedures. In many cases, particularly during surgical procedures, blood, mucus and other fluids in the area adjacent the distal end of the sheath of an endoscopic device can severely limit and impair the visibility which can be achieved with the telescopic portion of the device. Hence it is important that, whenever possible, effective irrigation and drainage be provided in the areas being treated in order to provide optimum visibility. In addition, however, it is also important that the irrigation and drainage of these areas be precisely controlled in order to avoid causing damage to the organs or tissue in these areas. In this regard, many conventional endoscopic devices have included means for effecting irrigation and drainage through the sheath portions thereof. They have also included both irrigation and drainage valves adjacent the proximal ends of the sheaths thereof, which are separately connectable to irrigation and drainage systems for supplying irrigation solutions to the instruments and for draining fluids therefrom. Unfortunately, however, the irrigation and drainage valves which have been utilized in conventional devices of this type have generally required substantial amounts of manipulation by operators thereof in order to effect irrigation and drainage, and hence it has generally been difficult to precisely control the amounts of fluids which are passed into or removed from the areas being treated utilizing devices of this type. This is particularly significant when it is recognized that in most cases the attention of operators of devices of this type must be constantly directed to the areas being treated and cannot safely be interrupted for the performance of mechanical manipulations, such as the opening and closing of drainage and irrigation valves.

While it is important that endoscopic devices include some means for effectively irrigating and draining fluids from areas of the body upon which surgical procedures are being carried out, a particular problem is presented when carrying out surgical procedures in the ureter. In this regard, unlike the bladder, the kidney and the ureter have limited volume capacities, and the kidney is very susceptible to injury from excess fluid volume and pressure. Nevertheless, it is generally necessary to irrigate and drain the ureter and kidney during endoscopy, particularly when surgical procedures are involved, because of the problems of visual impairment due to blood, mucus or debris due to pathological processes. Hence, while it is generally necessary to pass fluids into and out of the ureter and kidney during the performance of endoscopic procedures therein, the quantities of fluids which are passed into and out of the ureter and kidney must be precisely controlled in order to avoid serious damage to the ureter and/or the kidney.

The instant invention provides an effective endoscopic device which can be embodied in various forms for endoscopy of various parts of the human body, including the ureter, and it includes means for effectively controlling the irrigation and drainage of fluids in the area of the body being treated. In this regard, the endoscopic device of the instant invention comprises an elongated tubular endoscopic sheath having distal and proximal ends, telescope means received in the sheath and operative from a point adjacent the proximal end of the sheath for viewing an area adjacent the distal end of the sheath, and a three-way valve mounted on the sheath adjacent the proximal end thereof. The sheath is dimensioned to be received in an area of the human body for performing an endoscopic procedure, and it is operative for conducting fluids from a point adjacent the distal end thereof to a point adjacent the proximal end thereof. The valve is mounted on the sheath adjacent the proximal end thereof, and it has irrigation and drainage ports therein, and it communicates with the interior of the sheath so that it is operative for regulating the flow of fluids between the irrigation and drainage ports and the interior of the sheath. Specifically, the valve has a movable valve element thereon, which is moveable in a single motion between sequential first, second, and third positions, wherein the irrigation port is in communication with the interior of the sheath, but the drainage port is closed, wherein both of the irrigation and drainage ports are closed, and wherein the drainage port is in communication with the interior of the sheath, but the irrigation port is closed, respectively. Hence, because the valve is operative with a single motion between the sequential first, second, and third positions thereof, the flow of fluids to and from the sheath can be precisely and easily controlled by an operator of the device while the operator is viewing an area of the body of a patient through the telescope portion of the device without requiring the operator to look away from the lens of the telescope portion. Hence, the device can be utilized for performing endoscopic operations in the ureter and in other delicate areas of the human body, where the flow of irrigation and drainage fluids must be precisely and delicately controlled in order to prevent damage. In the preferred embodiment of the device of the instant invention, the valve element is rotatable in a single direction for sequential movement between the first, second, and third positions of the valve, and the valve element is preferably mounted on the top portion of the device so that it is easily operable. Further, the valve element is preferably formed with knurls thereon, and it is operative between the first, second, and third positions of the valve by rotating it less than one complete revolution. Accordingly, the valve can be operated by an operator by moving a forefinger along the knurled surface of the valve element on the upper portion of the device to cause the valve element to rotate, and because of the simplicity of this operation, the valve can be operated without distracting the operation's attention from the telescope portion of the device. The endoscopic device of the instant invention is preferably embodied as a ureteroscope and the sheath is preferably embodied as an elongated ureteroscopic sheath having a main portion which includes the proximal end of the sheath and is dimensioned for insertion into a patient so that it extends through the urethra and substantially through the bladder of the patient, and a reduced terminal portion which includes the distal end of the sheath and is dimensioned to be received in the ureter of the patient. Accordingly, when the device is installed in a patient, the valve can be manipulated by an operator by moving a forefinger along the knurled surface of the valve element to effect rotation thereof and to thereby alternatively irrigate or drain fluids from the area of the ureter adjacent the distal end of the device, and because the valve is operable with a single movement of a forefinger, the amount of fluids which are passed into or drained from the ureter can be precisely and safely controlled by the operator. Accordingly, blood, mucus and debris can be flushed from the area of the ureter adjacent the distal end of the device to provide enhanced visualization of the ureter during the performance of surgical and/or diagnostic procedures therein.

Accordingly, it is a primary object of the instant invention to provide an endoscopic device which is operable for effectively controlling irrigation and drainage of the area adjacent the distal end of the device.

Another object of the instant invention is to provide an endoscopic device, wherein the flow of fluids utilized for irrigation and drainage can be controlled with a single movement of a forefinger of an operator of the device.

Another object of the instant invention is to provide an effective uteroscope, wherein the flow or fluids passing into and out of the ureter for irrigation and drainage can be effectively controlled.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is an exploded perspective view of the endoscopic device of the instant invention;

FIG. 2 is an exploded perspective view of the valve portion thereof;

FIG. 3 is a plan view illustrating the operation of the valve portion of the device by an operator while the operator is looking through the telescope portion of the device;

DESCRIPTION OF THE INVENTION

Figure 4:
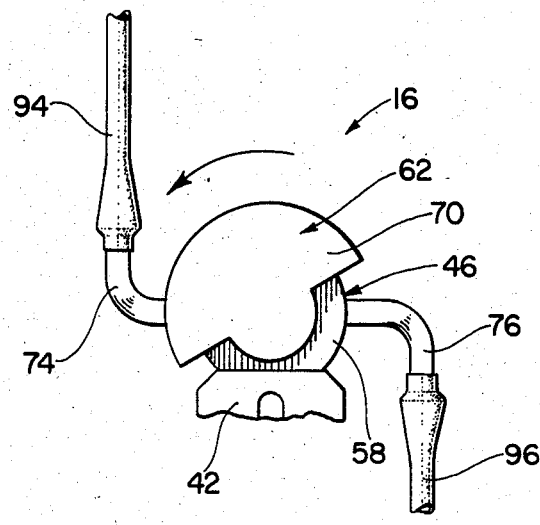
FIG. 4 is a rear elevational view of the valve portion of the device in the irrigating position.

Referring now to the drawing, the endoscopic device of the instant invention is illustrated in FIGS. 1 and 3 and generally indicated at 10. The endoscopic device 10 comprises an elongated tubular sheath generally indicated at 12, a telescope portion generally indicated at 14, and a valve-bridge assembly generally indicated at 16. The sheath 12 has distal and proximal ends 18 and 20, respectively, and the valve-bridge assembly 16 is detachably secured on the proximal end 20. The telescope portion 14 is detachably secured on the valve-bridge assembly 16 so that it extends therethrough and so that a portion thereof is received in the sheath 12. The device 10 is receivable in a patient for performing various diagnostic and surgical procedures. More specifically, the device 10 which is herein embodied as a ureteroscope, is receivable in a patient so that it extends through the urethra, through the bladder, and into the lower portion of the ureter of the patient, and it is operable by an operator 22 as illustrated in FIG. 3 by looking into the telescope portion 14 in order to view the area of the body of the patient which is adjacent the distal end 18. During this procedure, the valve-bridge assembly 16 can be manipulated by the operator 22 to control the irrigation and drainage of fluids from the area of the body of the patient adjacent the distal end 18 in order to provide improved visibility with the telescope portion 14.

The sheath 12, which is herein embodied as a ureterscope sheath, comprises an elongated tubular member having a main portion 24 which includes the proximal end 20 of the sheath 12 and a reduced terminal portion 26 which includes the distal end 18 and is integrally interconnected to the main portion 24 at a tapered intersection 28. The sheath 12 is dimensioned to loosely receive the telescope portion 14 therein so that there is sufficient room in the tubular interior of the sheath to conduct fluids between the distal and proximal ends 18 and 20, respectively, thereof for irrigation and drainage operations which will hereinafter be more fully described. The sheath 12 further comprises a coupling piece generally indicated at 30 for interconnecting the sheath 12 to the valve-bridge assembly 16. In this regard, the coupling piece 30 comprises a female body portion 32 which is attached to the main sheath portion 24 and a locking ring 34 having a pair of inwardly facing alignment notches 36 therein. The coupling piece 30 further includes a male coupling portion 38 which extends from the female body portion 32 a short distance along the main sheath portion 24 and has a pair of radially outwardly extending alignment pins 40 on opposite sides thereof. The main female body portion 32 and the ring 34 are operative for receiving and securing the valve-bridge assembly 16 to the sheath 12, whereas the male portion 38 is operative for receiving and securing a secondary sheath (not shown) thereon of larger diameter than the sheath 12 so that the sheath 12 extends through the secondary sheath.

The valve-bridge assembly 16 comprises a bridge element 42 having an aperture 44 therethrough, a three-way valve unit generally indicated at 46, which is mounted on the bridge element 42, an accessory block 48 which is mounted on the underside of the bridge element 42, and a male coupling element 50 having a pair of pins 52 which extend radially outwardly from opposite sides thereof. The aperture 44 extends through the male coupling element 50 as well as the bridge element 42 and the coupling element 50 is receivable in the female body portion 32 so that the pins 52 are received in the notches 36, whereupon the ring 34 is rotatable a slight amount to lock the valve-bridge assembly 16 on the sheath 12 adjacent the proximal end 20. When the valve-bridge assembly 16 is received on the sheath 12 in this manner, the aperture 44 is aligned with the tubular interior of the sheath 12. The accessory block 48 includes an accessory tube 54 having a removable cap 56 thereon, the tube 54 communicating with the aperture 44 for passing accessories therethrough into the sheath 12.

Figure 5:
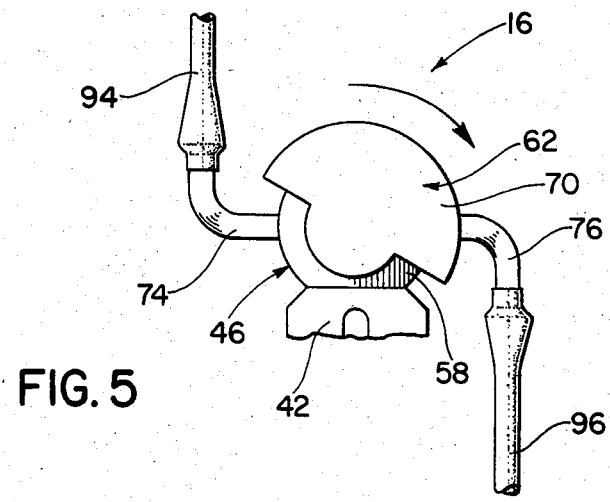
FIG. 5 is a rear elevational view of the valve portion in the draining position.

The valve unit 46 is more clearly illustrated in FIGS. 2, 4, and 5, and it comprises a cylindrical outer housing 58 having a slightly tapered axial bore 60 therein which extends partially through the housing 58 from the rear or proximal end thereof, and a valve element 62 having a slightly tapered plug 64 which is snugly but rotatably received in the bore 60. A threaded stud 66 extends from the forward or distal end of the plug 64, through an aperture (not shown) in the forward or distal end of the housing 58 and a nut 68 is received on the stud 66 for securing the plug 64 in the housing 58. The valve element 62 further comprises a semicircular knob portion 70 which is disposed rearwardly of the plug 64 and has knurls 72 thereon for rotating the valve element 62 in the housing 58. Extending upwardly and downwardly from opposite sides of the body 58 are tubular irrigation and drainage fittings 74 and 76, respectively, which communicate with irrigation and drainage ports 78 and 80, respectively, in the body 58, and a bridge port 82 provides communication between the bore 60 and the aperture 44. A tubular passage 84 is provided in the plug 64, and it is configured and oriented so that it can be positioned in a first position wherein it provides communication between the port 78 and the port 82, a second position wherein both the ports 78 and 80 are closed or blocked off by the plug 64, or a third position wherein the passage 84 provides communication between the port 80 and the port 82. In this regard, when the valve element 62 is moved to the first position thereof illustrated in FIG. 4, wherein it is rotated toward the irrigation fitting 74, the passage 84 provides communication between the ports 78 and 82 so that an irrigation fluid, such as a saline solution, can be passed through the fitting 74 and into the sheath 12, whereas when the valve element 62 is moved to the third position thereof illustrated in FIG. 5, wherein it is rotated toward the drainage fitting 76, the passage 84 provides communication between the ports 80 and 82 in order to drain fluids from an area adjacent the distal end 18 through the fitting 76. When the valve element 62 is positioned in the second or center position thereof, wherein the knob portion 70 is located in a centered or top position, the plug 64 blocks or closes off both of the ports 78 and 80. In any event, because of the configuration of the valve unit 46, an operator can easily rotate the valve element 62 by passing a forefinger over the knurls 72 as illustrated in FIG. 3 to move the valve element 62 between the first, second, and third positions thereof in a single movement. In this connection, it should also be pointed out that other embodiments of the endoscopic device of the instant invention which include other types of valves which are operative with a single motion between corresponding first, second, and third positions are also contemplated.

The telescope portion 14 comprises an endoscopic lens of conventional construction which is dimensioned to be used in combination with the valve-bridge assembly 16 and the sheath 12. The telescope portion 14 comprises a lens unit 86 having an eye piece 88, an elongated shaft 90, and a light carrier post 92 which is connectable to a light source for providing illumination to the telescope portion 14. The telescope portion 14 is receivable in the aperture 44 and in the sheath 12 for providing direct visual communication between the distal end 18 and the eye piece 88.

For use and operation of the device 10 which is herein embodied as a ureteroscope, it is installed in a patient so that the main portion 24 of the sheath 12 extends through the urethra and substantially through the bladder of the patient and so that the reduced terminal portion 26 is received in the lower portion of the patient's ureter. The irrigation fitting 74 is connected to a supply tube 94 for supplying a fluid, such as saline solution to the valve-bridge assembly 16, and a drainage tube 96 is connected to the tubular fitting 76. An operator of the device 10 can then observe the area of the ureter adjacent the distal end 18 while simultaneously effecting irrigation and drainage thereof. The valve 46 can be easily manipulated with a forefinger in the manner illustrated in FIG. 3 by passing the forefinger over the knurls 72 to rotate the valve element 62 between the three positions hereinabove described. Further, because this operation can be effected with a single movement of the forefinger in a single direction, it is possible for the operator 22 to carry out irrigation and drainage operations without interrupting visual contact with the ureter. In addition, because of the simplicity of the operation of the device 10, the amount of fluids which are passed into and drained from the ureter can be accurately and precisely controlled to avoid damage to the ureter and kidney.

It is seen, therefore that the instant invention represents a significant advancement in the medical art. In particular, the device 10 can be effectively utilized for endoscopically carrying out diagnostic and surgical procedures, and the valve unit 46 can be effectively utilized to effect irrigation and drainage during such operations. Further, because of the simplicity of the operation of the valve unit 46, it can be operated without requiring interruption of visual contact with the areas adjacent the distal end 18 and the amounts of fluids which are passed into or drained from these areas can be precisely controlled. Hence, for these reasons as well as the other reasons hereinabove set forth, it is seen that the instant invention represents a significant advancement in the medical art which has substantial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An endoscopic device comprising an elongated tubular endoscopic sheath which has distal and proximal ends and is operative for conducting fluids between a point adjacent the distal end thereof and a point adjacent the proximal end thereof, telescopic means received in said sheath and operative from a point adjacent the proximal end of said sheath for viewing an area adjacent the distal end of said sheath, and a valve mounted on said device adjacent the proximal end of said sheath, said valve having irrigation and drainage ports therein, communicating with the interior of said sheath and being operative for regulating the flow of fluids between said irrigation and drainage ports and the interior of said sheath, said valve having a movable valve element thereon and being operable by manually moving said valve element in a single motion between sequential first, second, and third positions wherein said irrigation port is in communication with the interior of said sheath, but said drainage port is closed, wherein said irrigation and drainage ports are both closed, and wherein said drainage port is in communication with the interior of said sheath, but said irrigation port is closed, respectively.

2. In the device of claim 1, said valve element being rotatable in a single direction for sequential movement of said valve between said first, second, and third positions.

3. In the device of claim 2, said valve element having knurls thereon, and being disposed on the top portion of said device, said valve being operable between said first, second, and third positions thereof by rotating said valve element by an amount less than one revolution whereby said valve can be operated between said first, second, and third positions thereof with a single movement of a forefinger of a user while the user is viewing through said telescopic means.

4. The device of claim 3 further characterized as a ureteroscope, said sheath further characterized as a ureteroscope sheath.

5. In the device of claim 4, said sheath comprising an elongated main portion which includes the proximal end of said sheath and is dimensioned for insertion into a patient so that it extends through the urethra and substantially through the bladder of said patient and a reduced terminal portion which includes the distal end of said sheath and is dimensioned to be received in the ureter of said patient, said valve being operable for effecting irrigation and drainage of the ureter of said patient when said distal end is received in said ureter.

* * * * *